US010921278B2

(12) United States Patent
Huang et al.

(10) Patent No.: US 10,921,278 B2
(45) Date of Patent: *Feb. 16, 2021

(54) SLOPE-BASED COMPENSATION INCLUDING SECONDARY OUTPUT SIGNALS

(71) Applicant: Ascensia Diabetes Care Holdings AG, Basel (CH)

(72) Inventors: Dijia Huang, Granger, IN (US); Huan-Ping Wu, Granger, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 346 days.

This patent is subject to a terminal disclaimer.

(21) Appl. No.: 15/986,539

(22) Filed: May 22, 2018

(65) Prior Publication Data

US 2018/0275089 A1    Sep. 27, 2018

Related U.S. Application Data

(63) Continuation of application No. 14/846,174, filed on Sep. 4, 2015, now Pat. No. 9,995,702, which is a
(Continued)

(51) Int. Cl.
*G01N 27/327* (2006.01)
*G01N 33/487* (2006.01)

(52) U.S. Cl.
CPC ... *G01N 27/3274* (2013.01); *G01N 33/48714* (2013.01)

(58) Field of Classification Search
CPC .................... G01N 27/3274; G01N 33/48714
(Continued)

(56) References Cited

U.S. PATENT DOCUMENTS 4,431,004 A    2/1984 Bessman
4,750,496 A    6/1988 Reinhart
(Continued)

FOREIGN PATENT DOCUMENTS

EP    1742045    1/2007
EP    1742054    1/2007
(Continued)

OTHER PUBLICATIONS

International Searching Authority, "International Search Report and Written Opinion for PCT/US2011/038329", dated Sep. 13, 2011, Publisher: European Patent Office.
(Continued)

*Primary Examiner* — Toan M Le
*Assistant Examiner* — Xiuqin Sun
(74) *Attorney, Agent, or Firm* — Nixon Peabody LLP

(57) ABSTRACT

A biosensor system determines analyte concentration from analytic and/or secondary output signals. The biosensor system adjusts a correlation for determining analyte concentrations from output signals with one or more index functions extracted from the output signals. The index functions determine at least one slope deviation or normalized slope deviation from one or more error parameters. The slope-adjusted correlation between analyte concentrations and output signals may be used to determine analyte concentrations having improved accuracy and/or precision from output signals including components attributable to bias.

20 Claims, 10 Drawing Sheets

Related U.S. Application Data continuation of application No. 13/117,872, filed on May 27, 2011, now Pat. No. 9,164,076.

(60) Provisional application No. 61/351,988, filed on Jun. 7, 2010.

(58) Field of Classification Search
USPC .......................................................... 702/19
See application file for complete search history.

(56) References Cited

U.S. PATENT DOCUMENTS

| | | | |
|---|---|---|---|
| 5,243,516 A | 9/1993 | White | |
| 5,366,609 A | 11/1994 | White | |
| 5,395,504 A | 3/1995 | Saurer | |
| 5,508,171 A | 4/1996 | Walling | |
| 5,620,579 A | 4/1997 | Genshaw | |
| 5,653,863 A * | 8/1997 | Genshaw | C12Q 1/004 |
| | | | 204/402 |
| 5,723,284 A | 3/1998 | Ye | |
| 5,798,031 A | 8/1998 | Charlton | |
| 6,120,676 A | 9/2000 | Heller | |
| 6,153,069 A | 11/2000 | Pottgen | |
| 6,233,471 B1 | 5/2001 | Berner | |
| 6,275,717 B1 | 8/2001 | Gross | |
| 6,391,645 B1 | 5/2002 | Huang | |
| 6,413,411 B1 | 7/2002 | Pottgen | |
| 6,475,372 B1 | 11/2002 | O'hara | |
| 6,576,117 B1 | 6/2003 | Iketaki | |
| 6,645,368 B1 | 11/2003 | Beaty | |
| 6,824,670 B2 | 11/2004 | Tokunaga | |
| 7,122,111 B2 | 10/2006 | Tokunaga | |
| 7,132,041 B2 | 11/2006 | Deng | |
| 7,338,639 B2 | 3/2008 | Burke | |
| 7,351,323 B2 | 4/2008 | Iketaki | |
| 7,491,310 B2 | 2/2009 | Okuda | |
| 7,501,052 B2 | 3/2009 | Iyenga | |
| 7,517,439 B2 | 4/2009 | Harding | |
| 7,781,222 B2 | 8/2010 | Wu | |
| 8,744,776 B2 | 6/2014 | Wu | |
| 9,995,702 B2 * | 6/2018 | Huang | G01N 27/3274 |
| 2004/0072158 A1 | 4/2004 | Henkens | |
| 2004/0079652 A1 | 4/2004 | Vreke | |
| 2004/0256248 A1 | 12/2004 | Burke | |
| 2004/0260511 A1 | 12/2004 | Burke | |
| 2005/0176153 A1 | 8/2005 | O'hara | |
| 2007/0045127 A1 * | 3/2007 | Huang | C12Q 1/006 |
| | | | 205/777.5 |
| 2007/0231914 A1 * | 10/2007 | Deng | G01N 27/3274 |
| | | | 436/70 |
| 2008/0248581 A1 * | 10/2008 | Chu | G01N 33/721 |
| | | | 436/66 |
| 2009/0177406 A1 * | 7/2009 | Wu | G01N 33/66 |
| | | | 702/19 |
| 2009/0236237 A1 * | 9/2009 | Shinno | G01N 33/54393 |
| | | | 205/792 |

FOREIGN PATENT DOCUMENTS

| | | |
|---|---|---|
| JP | 2005147990 | 6/2005 |
| JP | 2005156316 | 6/2005 |
| JP | 2009528540 | 8/2009 |
| RU | 2305279 | 8/2007 |
| WO | WO 1996/014026 | 5/1996 |
| WO | WO 1997/018464 | 5/1997 |
| WO | WO 1998/058250 | 12/1998 |
| WO | WO 2001/021827 | 3/2001 |
| WO | WO 2006/042304 | 4/2005 |
| WO | WO 2006/079797 | 8/2006 |
| WO | WO 2007/013915 | 2/2007 |
| WO | WO 2007/014231 | 2/2007 |
| WO | WO 2007/040913 | 4/2007 |
| WO | WO 2007/133985 | 11/2007 |
| WO | WO 2009/108239 | 9/2009 |
| WO | WO 2010/077660 | 7/2010 |

OTHER PUBLICATIONS

Gunasingham, et al., "Pulsed Amperometric Detection of Glucose Using a Mediated Enzyme Electrode", Journal of Electroanalytical Chemistry, 1990, pp. 349-362, vol. 287, No. 2.

Lin, et al., "Reduction of the Interferences of Biochemicals and Hematrocrit Ratio on the Determination of Whole Blood Glucose Using", "Anal. Bioanal. Chem.", 2007, pp. 1623-1631, vol. 289.

Panteleon, et al., "The Role of the Independent Variable to Gluscose Sensor Calibration", "Diabetes Technology & Therapeutics", 2003, pp. 401-441, vol. 5, No. 3.

* cited by examiner

SLOPE-BASED COMPENSATION INCLUDING SECONDARY OUTPUT SIGNALS

REFERENCE TO RELATED APPLICATIONS

This application is a continuation of U.S. Ser. No. 14/846,174 filed on Sep. 4, 2015; which is a continuation of U.S. Ser. No. 13/117,872 filed on May 27, 2011 and claims the benefit of U.S. Provisional Application No. 61/351,988 entitled "Slope-Based Compensation Including Secondary Output Signals" filed Jun. 7, 2010, all of which are incorporated by reference in their entireties.

BACKGROUND

Biosensor systems provide an analysis of a biological fluid, such as whole blood, serum, plasma, urine, saliva, interstitial, or intracellular fluid. Typically, the systems include a measurement device that analyzes a sample contacting a test sensor. The sample usually is in liquid form and in addition to being a biological fluid, may be the derivative of a biological fluid, such as an extract, a dilution, a filtrate, or a reconstituted precipitate. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor system to determine the glucose level in whole blood for adjustments to diet and/or medication.

Biosensor systems may be designed to analyze one or more analytes and may use different volumes of biological fluids. Some systems may analyze a single drop of whole blood, such as from 0.25-15 microliters (µL) in volume. Biosensor systems may be implemented using bench-top, portable, and like measurement devices. Portable measurement devices may be hand-held and allow for the identification and/or quantification of one or more analytes in a sample. Examples of portable measurement systems include the Ascensia® Breeze® and Elite® meters of Bayer HealthCare in Tarrytown, N.Y., while examples of bench-top measurement systems include the Electrochemical Workstation available from CH Instruments in Austin, Tex.

In electrochemical biosensor systems, the analyte concentration is determined from an electrical signal generated by an oxidation/reduction or redox reaction of the analyte or a species responsive to the analyte when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles. An enzyme or similar species may be added to the sample to enhance the electron transfer from a first species to a second species during the redox reaction. The enzyme or similar species may react with a single analyte, thus providing specificity to a portion of the generated output signal. A mediator may be used to maintain the oxidation state of the enzyme.

Electrochemical biosensor systems usually include a measurement device having electrical contacts that connect with electrical conductors in the test sensor. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The measurement device applies an input signal through the electrical contacts to the electrical conductors of the test sensor. The electrical conductors convey the input signal through the electrodes into the sample present in the sample reservoir. The redox reaction of the analyte generates an electrical output signal in response to the input signal. The electrical output signal from the strip may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the biological fluid.

In coulometry, a potential is applied to the sample to exhaustively oxidize or reduce the analyte. A biosensor system using coulometry is described in U.S. Pat. No. 6,120,676. In amperometry, an electrical signal of constant potential (voltage) is applied to the electrical conductors of the test sensor while the measured output signal is a current. Biosensor systems using amperometry are described in U.S. Pat. Nos. 5,620,579; 5,653,863; 6,153,069; and 6,413,411. In voltammetry, a varying potential is applied to a sample of biological fluid. In gated amperometry and gated voltammetry, pulsed inputs may be used as described in WO 2007/013915 and WO 2007/040913, respectively.

In many biosensor systems, the test sensor may be adapted for use outside, inside, or partially inside a living organism. When used outside a living organism, a sample of the biological fluid may be introduced into a sample reservoir in the test sensor. The test sensor may be placed in the measurement device before, after, or during the introduction of the sample for analysis. When inside or partially inside a living organism, the test sensor may be continually immersed in the sample or the sample may be intermittently introduced to the strip. The test sensor may include a reservoir that partially isolates a volume of the sample or be open to the sample. When open, the strip may take the form of a fiber or other structure placed in contact with the biological fluid. Similarly, the sample may continuously flow through the strip, such as for continuous monitoring, or be interrupted, such as for intermittent monitoring, for analysis.

Biosensor systems may provide an analytic output signal during the analysis of the biological fluid that includes one or multiple errors. These errors may be reflected in an abnormal output signal, such as when one or more portions or the entire output signal is non-responsive or improperly responsive to the analyte concentration of the sample. These errors may be from one or more contributors, such as the physical characteristics of the sample, the environmental aspects of the sample, the operating conditions of the system, and the like. Physical characteristics of the sample include hematocrit (red blood cell) concentration, interfering substances, and the like. Interfering substances include ascorbic acid, uric acid, acetaminophen, and the like. Environmental aspects of the sample include temperature and the like. Operating conditions of the system include underfill conditions when the sample size is not large enough, slow-filling of the sample, intermittent electrical contact between the sample and one or more electrodes in the sensor strip, degradation of the reagents that interact with the analyte, and the like. There may be other contributors or a combination of contributors that cause errors.

The analytic output signal is used by the biosensor system to determine the analyte concentration of the sample. In addition to analytic output signals, secondary output signals may be determined from the sample or otherwise and be used by the biosensor system to reduce errors in the analysis. Such secondary output signals may be determined from the electrodes used to determine the analyte concentration of the sample, or from additional electrodes. Additional electrodes may include the same reagent composition as the electrodes used to determine the analyte concentration of the sample, a different reagent composition, or no reagent composition. Secondary output signals also may be determined from thermocouples and the like. For example, a reagent composition may be used that reacts with an interferent or an electrode lacking reagent composition may be used to study one or more physical characteristics of the sample, such as whole blood hematocrit.

The measurement performance of a biosensor system is defined in terms of accuracy and/or precision. Increases in accuracy and/or precision provide for an improvement in measurement performance, a reduction in the bias, of the system. Accuracy may be expressed in terms of bias of the sensor system's analyte reading in comparison to a reference analyte reading, with larger bias values representing less accuracy. Precision may be expressed in terms of the spread or variance of the bias among multiple analyte readings in relation to a mean. Bias is the difference between one or more values determined from the biosensor system and one or more accepted reference values for the analyte concentration in the biological fluid. Thus, one or more errors in the analysis results in the bias of the determined analyte concentration of a biosensor system.

Bias may be expressed in terms of "absolute bias" or "percent bias". Absolute bias may be expressed in the units of the measurement, such as mg/dL, while percent bias may be expressed as a percentage of the absolute bias value over the reference value. Under the ISO standard (ISO-2003E), absolute bias is used to express error in glucose concentrations less than 75 mg/dL, while percent bias is used to express error in glucose concentrations of 75 mg/dL and higher. The term "combined bias" (expressed as bias/%-bias) represents absolute bias for glucose concentrations less than 75 mg/dL and percent bias for glucose concentrations of 75 mg/dL and higher. Accepted reference values for analyte concentrations may be obtained with a reference instrument, such as the YSI 2300 STAT PLUS™ available from YSI Inc., Yellow Springs, Ohio.

Hematocrit bias refers to the difference between the reference glucose concentration obtained with a reference instrument and an experimental glucose reading obtained from a biosensor system for samples containing differing hematocrit levels. The difference between the reference and values obtained from the system results from the varying hematocrit level between specific whole blood samples and may be generally expressed as a percentage by the following equation: % Hct-Bias=$100\% \times (G_m - G_{ref})/G_{ref}$, where $G_m$ and $G_{ref}$ are the determined glucose and reference glucose concentration readings, respectively, for any hematocrit level. The larger the absolute value of the % Hct-bias, the more the hematocrit level of the sample (expressed as % Hct: the percentage of red blood cell volume/sample volume) is reducing the accuracy and/or precision of the determined glucose concentration.

For example, if whole blood samples containing identical glucose concentrations, but having hematocrit levels of 20, 40, and 60%, are analyzed, three different glucose readings will be reported by a system based on one set of calibration constants (slope and intercept of the 40% hematocrit containing whole blood sample, for instance). Thus, even though the whole blood glucose concentrations are the same, the system will report that the 20% hematocrit whole blood sample contains more glucose than the 40% hematocrit whole blood sample, and that the 60% hematocrit whole blood sample contains less glucose than the 40% hematocrit whole blood sample. "Hematocrit sensitivity" is an expression of the degree to which changes in the hematocrit level of a sample affect the bias values for an analysis. Hematocrit sensitivity may be defined as the numerical values of the combined biases per percent hematocrit, thus bias/%-bias per % Hct.

Many biosensor systems include one or more methods to correct errors associated with an analysis. The concentration values obtained from an analysis with an error may be inaccurate. Thus, the ability to correct these analyses may increase the accuracy and/or precision of the concentration values obtained. An error correction system may compensate for one or more errors, such as a sample temperature or a sample hematocrit level, which are different from a reference temperature or a reference hematocrit value.

While conventional error compensation systems balance various advantages and disadvantages, none are ideal. Conventional systems usually are directed to detect and respond to a particular type of error, either temperature or hematocrit, for example. Such systems typically do not have the ability to compensate for multiple error sources or to use both analytic and secondary output signals for compensation. These systems generally also lack the ability to alter the compensation for the error based on the output signal from a specific sample. Consequently, conventional biosensor systems may provide analysis results having determined analyte concentration values outside a desired measurement performance limit.

Accordingly, there is an ongoing need for improved biosensor systems, especially those that may provide increasingly accurate and/or precise determination of the concentration of the analyte in the sample. The systems, devices, and methods of the present invention overcome at least one of the disadvantages associated with conventional biosensor systems.

SUMMARY

The present invention provides a biosensor system that adjusts a relation for determining analyte concentrations in a biological sample from analytic and/or secondary output signals with one or more index function responsive to one or more errors that could bias the determined analyte concentrations. The bias may be represented by slope deviations and normalized slope deviations obtained from one or more error parameters. The slope deviations may be determined with one or more index functions from the error parameters. The term or terms of the index functions may include error parameters extracted from or independent of the analytic output signals.

In a method for determining an analyte concentration in a sample, an output signal responsive to the concentration of the analyte in the sample is generated. At least one slope deviation from at least one error parameter is determined, and the analyte concentration of the sample is determined from the at least one analytic output signal and at least one slope compensation equation. The slope compensation equation is responsive to at least one index function and includes at least one reference correlation and at least one slope deviation. The slope compensation equation may be used to determine the analyte concentration of the sample by correcting an analyte concentration determined without the slope compensation equation with the slope compensation equation. The analyte concentration of the sample may be determined by adjusting a correlation relating the analytic output signal to the analyte concentration in the biological sample with the slope compensation equation. The analyte concentration of the sample may be determined by adjusting the at least one analytic output signal with the slope compensation equation. The at least one slope deviation may be determined from a predictor function f(predictor). The f(predictor) includes an index function and relates at least one error parameter to the slope deviation value. The reaction may be an electrochemical redox reaction.

A biosensor system for determining an analyte concentration in a sample includes a measurement device and a test sensor. The measurement device has a processor connected to a sensor interface and to a storage medium. The test sensor has a sample interface adjacent to a reservoir formed by the sensor. The processor determines an output signal value responsive to the concentration of the analyte in the sample from the sensor interface. The processor determines at least one slope deviation value from an error parameter and compensates the output signal value with the at least one slope deviation value and at least one reference correlation present in the storage medium.

A biosensor system adjusts a correlation between analyte concentrations and output signals with at least one slope deviation value in response to error parameters. The processor determines an analyte concentration from the slope-adjusted correlation in response to an output signal from the sample interface.

In another method for determining an analyte concentration in a sample, one or more output signals are generated from a sample. At least one complex index function is determined, where the complex index function is responsive to an error parameter obtained from a secondary output signal. The analyte concentration in the sample is determined from the output signals in response to the at least one complex index function.

Other systems, methods, features, and advantages of the invention will be, or will become, apparent to one with skill in the art upon examination of the following figures and detailed description. It is intended that all such additional systems, methods, features and advantages be included within this description and be within the scope of the invention.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

Figure 1A:
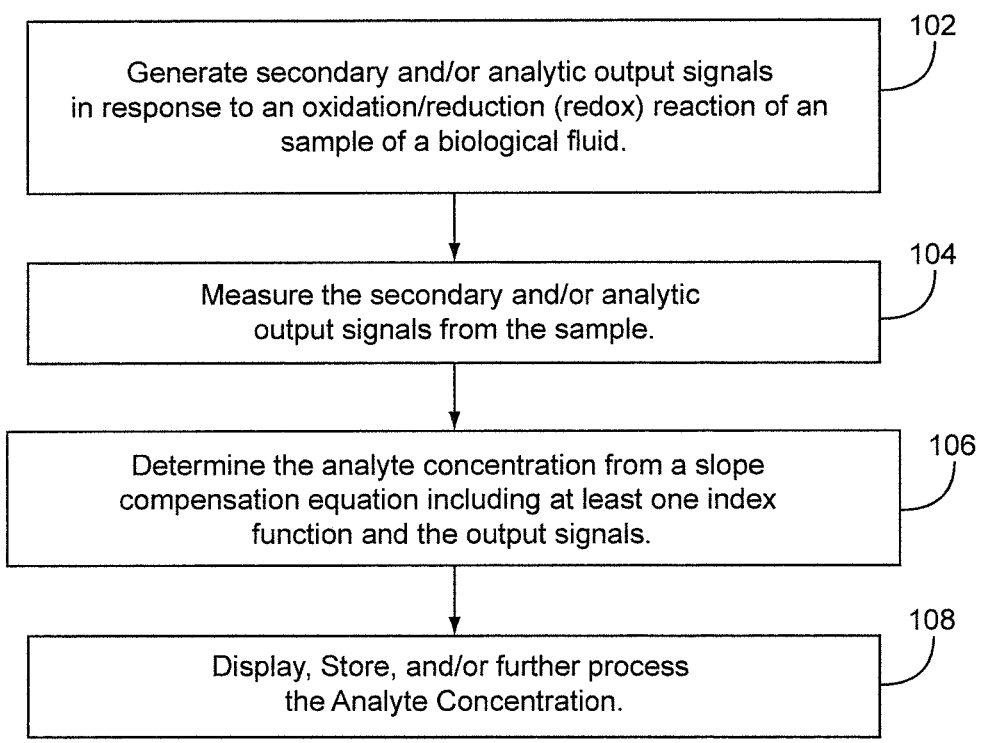
FIG. 1A represents a method for determining an analyte concentration in a sample.

A biosensor system adjusts a correlation for determining analyte concentrations in a biological sample from output signals with index functions extracted from intermediate signals of the analytic output signals and/or from secondary output signals. The intermediate signals may be one or more portions of the analytic output signals or the like. The secondary output signals are responsive to the physical or environmental characteristics of the biological sample. In addition to the compensation system providing substantial benefits when analyzing complex biological samples, the compensation system may be used to improve the measurement performance of other types of analysis.

The %-bias in the correlation of analyte concentrations with output signals may be represented by one or more slope deviations obtained from one or more error parameters. Error containing portions of output signals are reflected in the deviation between the hypothetical slope of the output signals and the slope of a reference correlation. By determining one or more values reflecting this deviation in slope from one or more error parameters, the measurement performance of an analysis may be increased. Predictor functions, index functions, and/or complex index functions correspond to the %-bias in the correlation between the analyte concentrations and the output signals due to one or more errors in the analysis.

Predictor functions compensate the measured analyte concentration for one or more errors in the analyte concentration analysis. Such errors can result in bias, thus reducing the accuracy and/or precision, of the determined analyte concentrations. One or more predictor functions may be used. A predictor function that perfectly correlates with the total slope deviation would provide an ultimate total error compensation of the analyte concentration. Such a hypothetical, perfectly correlated predictor function could be used to compensate for all errors in the analysis without having to know the exact cause of the total slope deviation, and thus the bias of the measured analyte concentration. Predictor functions include at least one index function, and one or more of the index functions may be complex.

An index function is responsive to at least one error parameter. An index function may be a calculated number that correlates with an error parameter, such as hematocrit or temperature, and represents the influence of this error parameter on bias. Index functions may be experimentally determined as a regression or other equation of the plot between the deviation from a reference slope and the error parameter. Thus, the index function represents the influence of the error parameter on the slope deviation. Complex index functions include combinations of terms modified by weighing coefficients. The terms included in the complex index function may be selected with one or more exclusion tests.

Error parameters may be any value responsive to one or more errors in the output signal. Error parameter may be values from the analysis of the analyte, such as the intermediate signals from an analytic output signal, or from secondary output signals independent of the analytic output signal, such as from thermocouple currents or voltages, additional electrode currents or voltages, and the like. Thus, the error parameters may be extracted directly or indirectly from the output signal of the analysis and/or obtained independently from the analytic output signal. Other error parameters may be determined from these or other analytic or secondary output signals. Any error parameter may be used to form the term or terms that make up the index function, such as those described in Intl. Pub. No. WO 2009/108239, filed Dec. 6, 2008, entitled "Slope-Based Compensation," and the like. A more detailed treatment of error correction using index functions and slope deviation values also may be found in this publication.

Slope deviations may be normalized to reduce the statistical effect of changes in the output signals, improve the differentiation in variations of the output signals, standardize the measurements of the output signals, a combination thereof, or the like. Since the slope deviation may be normalized, an index function also may be expressed in terms of the relation between slope deviation and the slope of the reference correlation. In normalization, the slope deviation, index function, or other parameter is adjusted (multiplied, divided, or the like) by a variable to reduce the statistical effect of changes in the parameter, improve the differentiation in variations of the parameter, standardize measurements of the parameter, a combination thereof, or the like. The greater the correlation between a predictor or index function and slope deviation, the better the function at correcting error in the analysis.

An index function is complex when the function includes a combination of terms modified by weighing coefficients. The combination is preferably a linear combination, but other combination methods may be used that provide weighing coefficients for the terms. Each term may include one or more error parameters. A more detailed treatment of using predictor and complex index functions for analyte analysis may be found in Intl. App. No. PCT/US2009/067150, filed Dec. 8, 2009, entitled "Complex Index Functions."

FIG. 1A represents a method for determining an analyte concentration in a sample of a biological fluid. In 102, the biosensor system generates secondary and/or analytic output signals in response to an oxidation/reduction (redox) reaction of an analyte in a sample of a biological fluid. In 104, the biosensor system measures the secondary and analytic output signals. In 106, the analyte concentration is determined from a slope compensation equation including at least one index function and the output signals. The slope compensation equation may be used with the at least one index function and the output signals to determine analyte concentrations in the sample from the output signals or alternatively may be used to correct analyte concentrations and may provide improved measurement performance in comparison to conventional biosensors. In 108, the analyte concentration may be displayed, stored for future reference, and/or used for additional calculations.

In 102 of FIG. 1A, the biosensor system generates analytic and secondary output signals in response to an oxidation/reduction (redox) reaction of an analyte in a sample of a biological fluid. The output signal may be generated using an electrochemical or optical sensor system.

In 104 of FIG. 1A, the biosensor system measures the secondary and/or analytic output signals. The system may measure the output signals continuously or intermittently. For example, the biosensor system may measure the analytic output signal intermittently during the pulses of a gated amperometric input signal, resulting in multiple current values recorded during each pulse. Secondary output signals may be measured before, during, or after the analytic output signals are measured. The system may show output signals on a display and/or may store one or more output signal or portions of the output signals in a memory device.

Figure 2A:
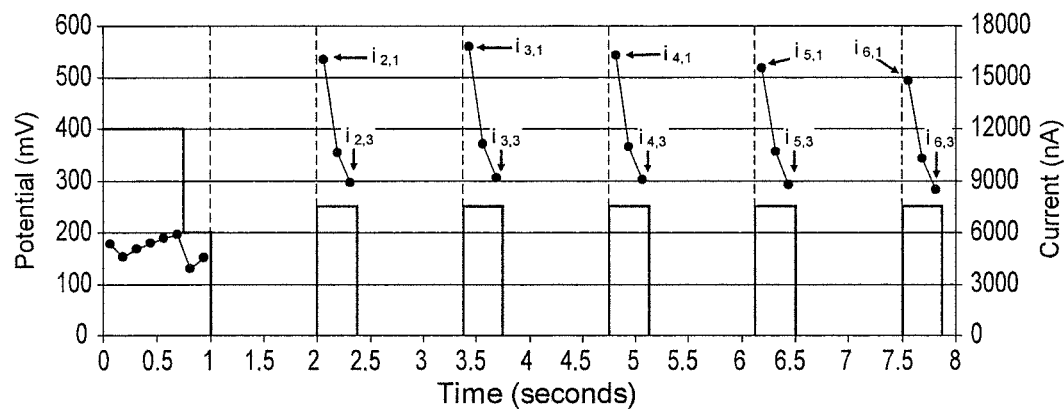
FIG. 2A represents a gated pulse sequence where the input signal applied to the working and counter electrodes includes multiple pulses.

FIG. 2A represents a gated pulse sequence where the input signal applied to the working and counter electrodes includes multiple pulses. The analytic output signal current values resulting from the pulses are depicted above each pulse. The intermediate signal current values are depicted as solid circles. Each of the i values is a current value of the analytic output signal responsive to the input signal. The first number in the subscript of the i values denotes the pulse number, while the second number in the subscript denotes the order of the output signal as the current values were measured. For example, $i_{2,3}$ denotes the third current value measured for the second pulse.

Index functions may include ratios extracted from the intermediate analytic output signals as depicted in FIG. 2A. For example, the intermediate signal values may be compared within an individual pulse-signal decay cycle, to provide inter-pulse ratios such as ratios $R3=i_{3,3}/i_{3,1}$, $R4=i_{4,3}/i_{4,1}$, and the like. In another example, the intermediate signal values may be compared between separate pulse-signal decay cycles, such as ratios $R3/2=i_{3,3}/i_{2,3}$, $R4/3=i_{4,3}/i_{3,3}$, and the like.

Index functions also may include combinations of ratios extracted from the analytic output signal depicted in FIG. 2A. In one example, an index function may include a ratio of ratios, such as Ratio3/2=R3/R2, Ratio4/3=R4/R3, and the like. In another example, an index function may include a combination of indices. For example, a combination index, Index-1, may be represented as Index-1=R4/3−Ratio3/2. In another example, a combination index Index-2 may be represented as Index-2=$(R4/3)^p$−$(Ratio3/2)^q$, where p and q independently are positive numbers.

Figure 2B:
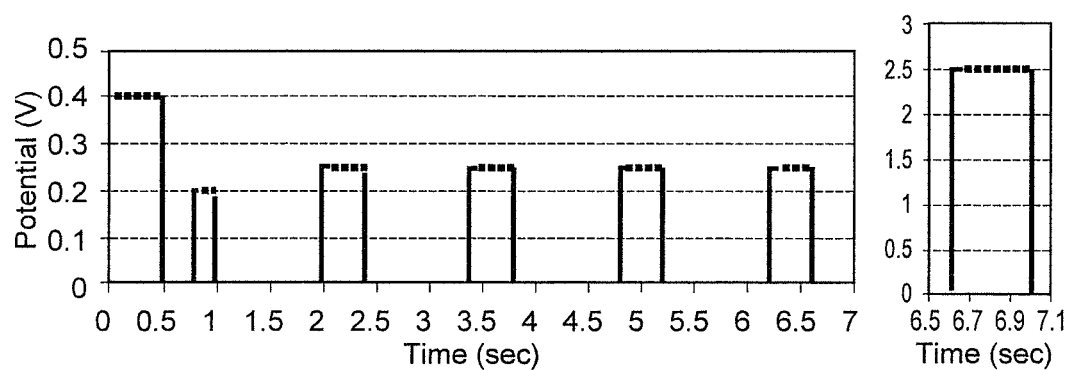
FIG. 2B represents a gated pulse sequence where the input signal applied to the working and counter electrodes includes multiple pulses, and where a second input signal is applied to an additional electrode to generate a secondary output signal.
Figure 2C:
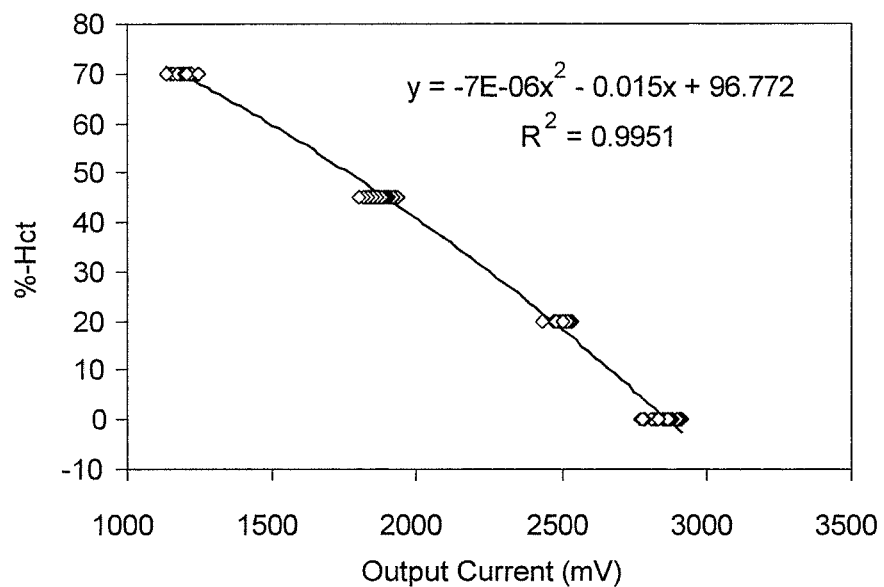
FIG. 2C depicts secondary output signal currents measured with an additional electrode from multiple blood samples including 0%, 20%, 45%, or 70% Hct.

FIG. 2B represents a gated pulse sequence where the input signal applied to the working and counter electrodes includes multiple pulses, and where a second input signal is applied to an additional electrode to generate a secondary output signal. The input signal applied to the additional electrode was applied after the completion of the analytic input signal, but could be applied at other times. FIG. 2C depicts secondary output signal currents measured with an additional electrode from multiple blood samples including 0%, 20%, 45%, or 70%-Hct. In this instance, the correlation is expressed in the form of a second order polynomial, but a linear or other correlation also may be used. For example, the secondary output signal current measured from the additional electrode of a test sensor including a blood sample with about 20%-Hct content was about 2500 mV. Thus, the current values from the additional electrode may be used in an index function relating the current values measured from the additional electrode to the %-Hct of the sample.

An example of a complex index function is represented as follows:

$$f(CIndex) = a_1 + (a_2)(Hct) + (a_3)(R4/3) + (a_4)(R5/4) + (a_5)(R6/5) + (a_6)(R6/4) + (a_7)(Hct)(G_{raw}) + (a_8)(R4/3)(G_{raw}) + (a_9)(R5/3)(G_{raw}) + (a_{10})(R6/5)(G_{raw}) + (a_{11})(R6/4)(G_{raw}) + (a_{12})(Temp)(Hct) + (a_{13})(Temp)(R5/3) + (a_{14})(Temp)(R6/5) + (a_{15})(Hct)(R5/4) + (a_{16})(Hct)(R6/5) + (a_{17})(Hct)(R6/4) + \ldots,$$

where $a_1$ is a constant, $a_2$-$a_{17}$ independently are weighing coefficients, $G_{raw}$ is the determined analyte concentration of the sample without compensation, Temp is temperature, and Hct is the current from an additional electrode. Each of the weighing coefficients ($a_2$-$a_{17}$) is followed by its associated term.

There are at least three basic types of terms in this complex index function: (1) the individual ratio indices extracted from the analytic output signal, such as R3/2 and R4/3, (2) the interaction terms between the ratio indices extracted from the analytic output signal and the temperature, Hct current, and/or $G_{raw}$, such as (Temp)(R5/3) and (R4/3)($G_{raw}$), and (3) temperature, Hct, or $G_{raw}$. The terms may include values other than error parameters, including $G_{raw}$. Other terms also may be used, including, but not limited to a combination index function, as previously described. The complex index function may be solved to provide a complex index value when the terms are replaced with the appropriate values. Statistical processing may be performed on the multiple terms to determine one or more constants and weighing coefficients. Statistical package software, including MINITAB (MINTAB, INC., State College, Pa.), may be used to perform the statistical processing.

The terms for inclusion in the complex index function may be selected using one or more mathematical techniques to determine exclusion values for each potential term. One or more exclusion tests are then applied to the exclusion values to identify terms to exclude from the complex index function. For example, p-values that indicate the probability of affecting the correlation between the complex index function and the slope deviation if the term were eliminated from the complex index function may be used as exclusion values under an exclusion test to exclude terms from the complex index function. Thus, removing terms from the complex index function that do not affect the correlation between the complex index function and the slope deviation in an undesirable way, allows the desired correlation between the complex index function and the slope deviation. A more detailed discussion of using exclusion values and tests to select terms for complex index functions may be found in Intl. App. No. PCT/US2009/067150, filed Dec. 8, 2009, entitled "Complex Index Functions."

The constant $a_1$ may be determined by regression or other mathematical technique. While a single constant is shown in the complex index function, a constant is not required; more than one may be used, and may be equal to 0. Thus, one or more constants may or may not be included in the complex index function. One or more constants also may be combined with the complex index function in forming a predictor function, such as a $b_0$ constant as subsequently described, for example.

While terms having weighing coefficients of one may be used, a complex index function includes at least two terms that are modified by weighing coefficients. Weighing coefficients are numerical values other than one or zero. Preferably, each term including an error parameter is modified by a weighing coefficient. More preferably, each non-constant term of the complex index function is modified by a weighing coefficient. Weighing coefficients may have positive or negative values. Weighing coefficients may be determined through the statistical processing of the experimental data collected from a combination of multiple analyte concentrations, different hematocrit levels, different temperatures, and the like.

As at least two of the terms are modified by weighting coefficients, different terms that are responsive to the same error type may be synergistically combined in the complex index function. For example, if R5/4 substantially describes the hematocrit content of the sample at high hematocrit (about 40% to about 70%), while the current value obtained from the additional electrode substantially describes the hematocrit content of the sample at low hematocrit (about 10% to about 40%), the weighting coefficients can assign the appropriate "blend" of these terms to provide the desired increase in measurement performance. Additionally, the ability of any one bad term, such as an incorrect reading from the additional electrode, to adversely affect the measurement performance of the analysis may be reduced.

In 106 of FIG. 1A, the analyte concentration of the sample may be determined from a slope compensation equation including at least one index function and the output signals. The index function may form part of a predictor function and may be complex. The index function may relate slope or intercept to an error parameter. Index functions, in addition to reference correlation equations, may be pre-determined and stored in the biosensor system. Error parameter values may be determined before, during, or after the analysis.

Figure 3A:
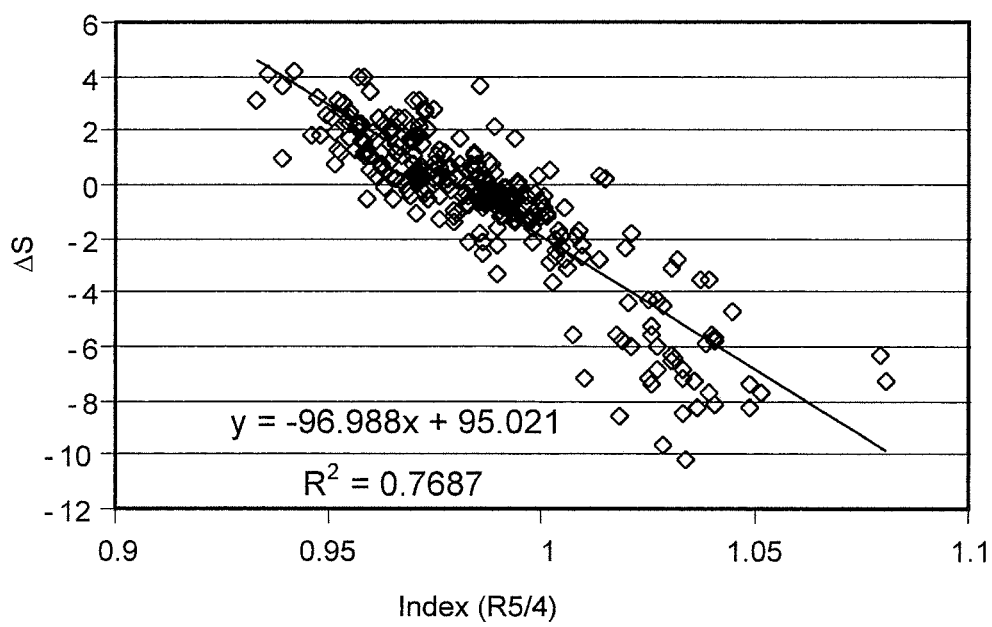
FIG. 3A depicts the correlation of $\Delta S$ with an index function responsive to the ratio index R5/4.
Figure 3B:
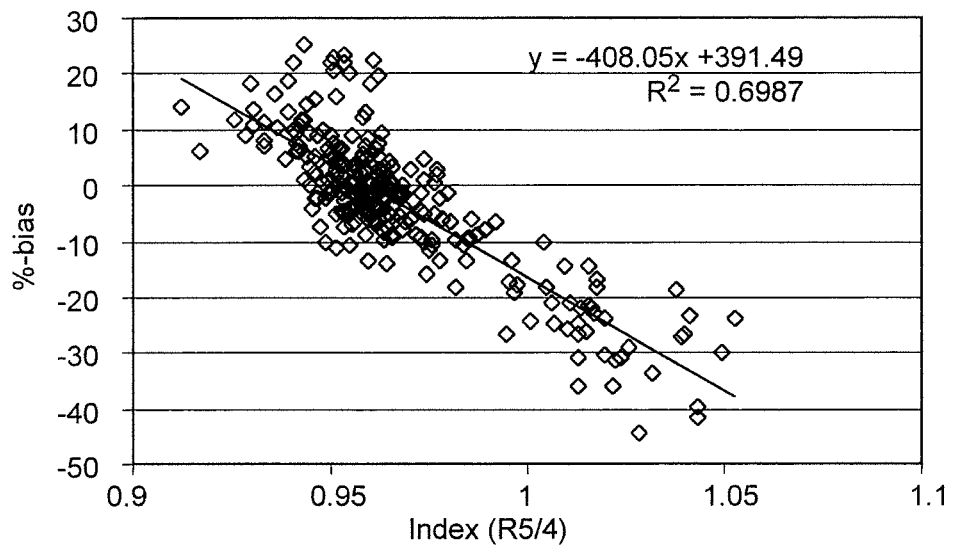
FIG. 3B depicts the correlation between %-bias and an index function relating a ratio error parameter (R5/4) to slope.

FIG. 3A depicts the correlation of ΔS with an index function responsive to the index R5/4 error parameter. FIG. 3B depicts the correlation between %-bias and the index R5/4, an error parameter, where the regression equation is the index function. In FIG. 3B, the ratio parameter R5/4 represents the relationship between the analytic output signal currents generated by the analyte in response to the $4^{th}$ and $5^{th}$ pulses of a gated amperometry pulse sequence including 7 pulses. The ratio error parameter R5/4 is an example of an error parameter determined from an analytic output signal.

Figure 3C:
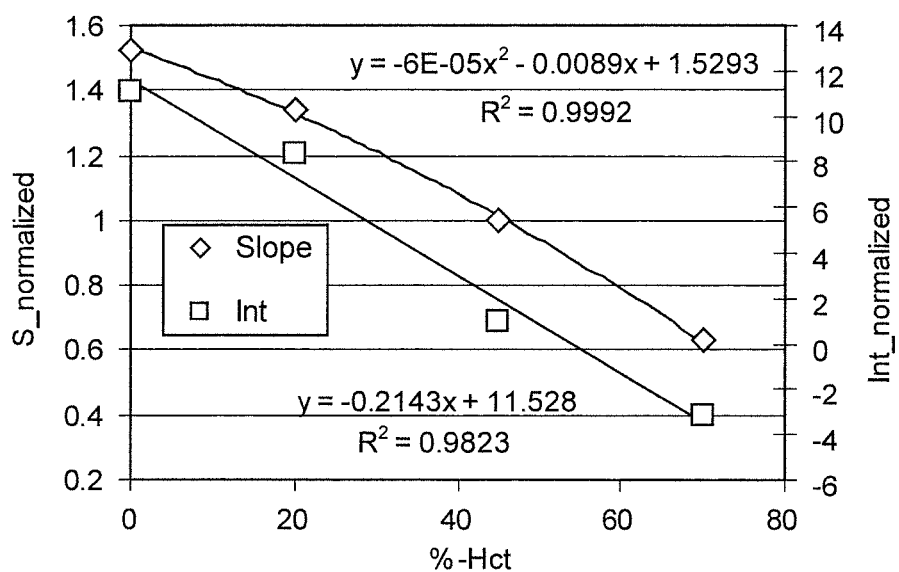
FIG. 3C depicts slope and intercept based index functions relating the error parameter of the secondary output signal currents measured from the additional electrode to the %-Hct of the sample.

FIG. 3C depicts slope and intercept based index functions relating the error parameter of the secondary output signal currents measured from the additional electrode to the %-Hct of the sample. The currents measured from the additional electrode are an example of an error parameter determined from a secondary output signal. Thus, FIG. 2C may be used to determine the %-Hct of a whole blood sample from the secondary output signal currents of the additional electrode, while the relationship of FIG. 3C may be used to determine the slope and intercept at different %-Hct.

Slope compensation equations use a slope deviation with analytic output signals to provide a compensated analyte concentration in a sample. The slope compensation equation may use at least one index function representing the slope deviation in combination with the analytic output signal values to provide a compensated analyte concentration. The slope compensation equation also may use other functions and/or values to represent the slope deviation. The slope compensation equation preferably compensates for error by adjusting a reference correlation between output signals and known analyte concentrations to provide a compensated or corrected analyte concentration.

As previously discussed with regard to FIG. 2C, a secondary output signal in the form of a current from an additional electrode may be considered an error parameter describing the hematocrit content of a whole blood sample. The hematocrit content of the sample may be considered an error parameter because an error in concentration values may arise from performing an analysis at a hematocrit content other than that at which the reference correlation was determined. The hematocrit content of the sample may be determined from any source, such as an electrode, calculated estimates, and the like. Thus, $f(Index)_{Hct}$ relates hematocrit sample content to the slope deviation between the reference correlation slope determined at a reference hematocrit content and the hypothetical slope of the line that would provide the hematocrit affected analyte concentration at the hematocrit content at which the analysis was performed. Similarly, $g(Index)_{Hct}$ relates hematocrit sample content to the deviation in intercept between the reference correlation intercept determined at a reference hematocrit content and the hypothetical intercept of the line that would provide the hematocrit affected analyte concentration at the hematocrit content at which the analysis was performed. The slope index function for hematocrit $f(Index)_{Hct}$ and/or the intercept index function for hematocrit $g(Index)_{Hct}$ may be stored in the biosensor system with the reference correlation equation.

A slope compensation equation using normalization with intercepts and hematocrit based index functions may take the form:

$$A_{corr} = (i - Int_{x\%-Hct})/S_{x\%-Hct} = (i - Int_{nml} * g(Index)_{Hct})$$
$$(S_{nml} * f(Index)_{Hct}) \quad \text{(Equation A)},$$

where $Int_{x\%-Hct}$ is intercept at x-% Hct, $S_{x\%-Hct}$ is slope at x-% Hct, $Int_{nml}$ is the normalized intercept, $g(Index)_{Hct}$ is the intercept based index function for %-Hct, $S_{nml}$ is the normalized slope, and $f(Index)_{Hct}$ is the slope based index function for %-Hct. Thus, index functions are used to relate hematocrit to both slope and intercept. This relationship expresses the slope deviation attributable to the hematocrit effect in the form of normalized slope $S_{nml} = S/S_{ref-Hct}$ with the addition of normalized intercept $Int_{nml} = Int/Int_{ref-Hct}$. The relationship also presumes %-Hct to be the only error source and normalization is with respect to the reference %-Hct. However, more than one error source is likely to cause the slope and intercept deviations. Therefore, the slope normalization is to the deviated slope, whether originating from hematocrit or other error sources, and is normalized by $S_{cal}$, the overall reference correlation slope.

Figure 4A:
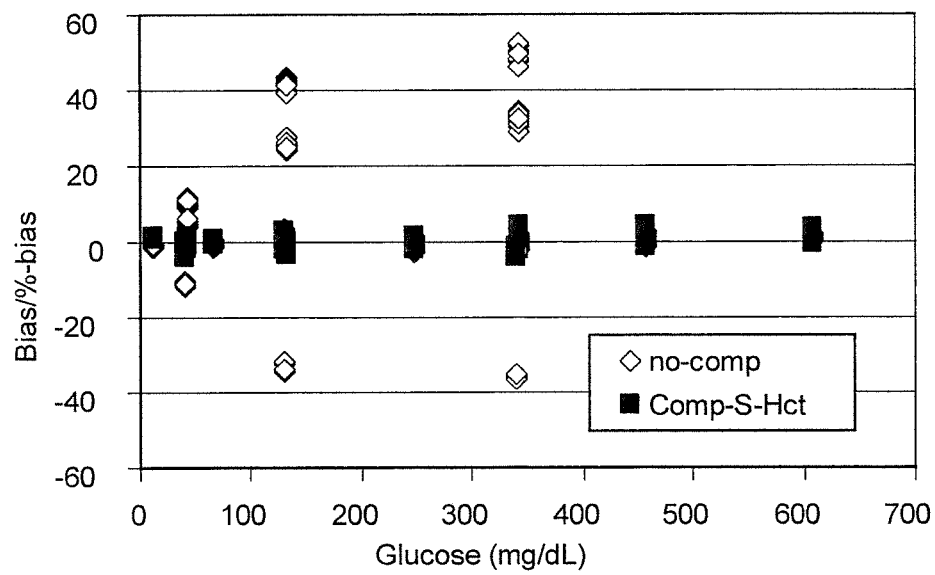
FIG. 4A shows the reduction in bias for multiple whole blood samples including different glucose concentrations and hematocrit contents of 0%, 20%, 45% and 70%-Hct.

FIG. 4A shows the reduction in the combined bias for multiple whole blood samples including different glucose concentrations and hematocrit contents of 0%, 20%, 45% and 70%-Hct. The current from the additional electrode was measured after about 5.7 seconds from the start of the analysis. The analyses were performed at about 25.3±0.5° C. and the 45%-Hct value was used as the center. In relation to Equation A, the following relationships were used:

$$S_{nml} = S_{x\%-Hct}/S_{45\%-Hct} = f(Index)_{Hct} = -6E-05(Hct)^2 - 0.0089(Hct) + 1.5293,$$

and $$Int_{nml} = Int_{x\%-Hct}/Int_{45\%-Hct} = g(Index)_{Hct} = -0.2143 * (Hct) + 11.528,$$

where (Hct) represent the output signals in mV from the additional electrode, and $S_{45\%-Hct}$ and $Int_{45\%-Hct}$ are the calibration slope and intercept at the selected center hematocrit of 45%-Hct. The compensation placed about 100% of the analyses within a ±10% combined bias limit at the ideal condition of 25° C. A combined bias limit is a performance limit reflecting the percentage of analyses falling within a selected boundary away from a reference value.

Figure 4B:
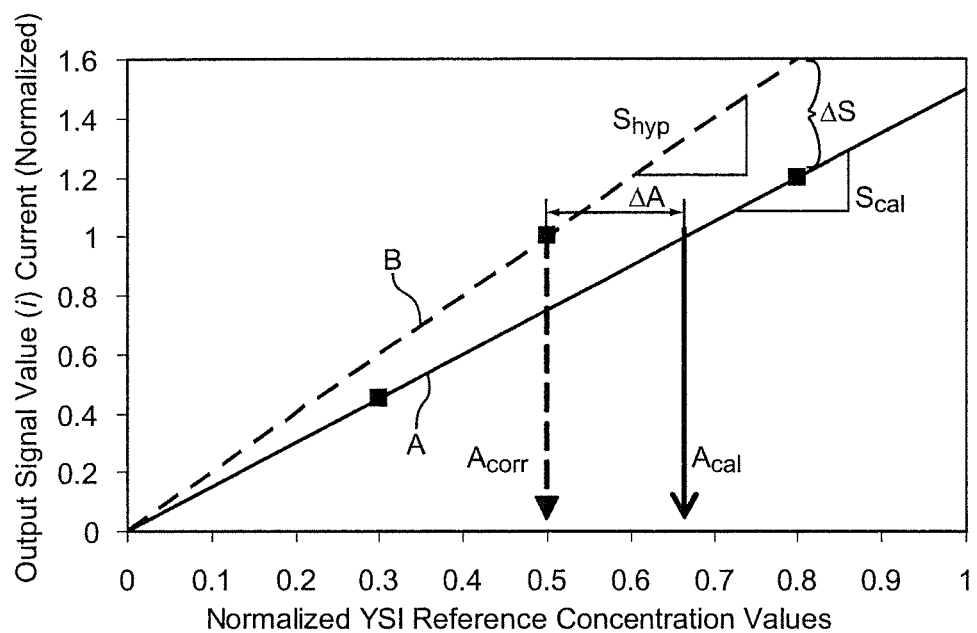
FIG. 4B depicts the relationship between $S_{cal}$, $S_{hyp}$, $\Delta S$, $\Delta_{corr}$, $A_{cal}$, and $\Delta A$.

For a biosensor system having a linear or near-linear relationship between analytic output signals and analyte concentration, system error may be simplified by combining errors into the slope deviation from the reference correlation. FIG. 4B shows the relationship between $S_{cal}$, $S_{hyp}$, $\Delta S$, $A_{corr}$, $A_{cal}$, and $\Delta A$. Line A represents a reference correlation having a slope $S_{cal}$ and relating an output signal in the form of current values from a biosensor system to analyte concentration values obtained from a YSI or other reference instrument for the samples. When used during the analysis of a sample by a biosensor system, the reference correlation of Line A may include analytic output signal current values having one or more errors that may provide an inaccurate and/or imprecise analyte concentration value. Line B represents an error-compensated correlation having a slope $S_{hyp}$ and relating current values obtained from the biosensor system with the sample analyte concentration values as obtained from the reference instrument. The error-compensated correlation has been adjusted or modified to reduce or substantially eliminate the one or more errors. $\Delta S$ is the slope deviation between these correlation lines and may be represented as a difference or by other mathematical operators. $\Delta A$ is the difference between the uncompensated or uncorrected ($A_{cal}$) and error compensated or corrected ($A_{corr}$) determined analyte concentration values.

Thus, a slope compensation equation using $\Delta S$ may be represented as follows:

$$A_{corr} = \frac{i - Int}{S_{cal} + \Delta S}, \quad \text{(Equation 1)}$$

where $A_{corr}$ is the corrected analyte concentration, i is a value of the output signal from a biosensor system, Int is the intercept from a reference correlation equation, $S_{cal}$ is the slope from the reference correlation equation, and $\Delta S$ represents the deviation in slope between $S_{cal}$ and a hypothetical slope of a line ($S_{hyp}$) for the analytic output signal value that provides an analyte concentration of the sample without error. The Int and $S_{cal}$ values for the reference correlation equation may be implemented as a program number assignment (PNA) table, another look-up table, or the like in the biosensor system. The equation may be simplified through normalization to eliminate the Int term. Other slope compensation equations including at least one slope deviation value and the analytic output signal may be used. While the equations presented throughout the application and claims may include an "=" sign, the sign is used to represent equivalence, relationship, prediction, or the like.

Without compensation or correction, a specific analytic output signal value will provide a different sample analyte concentration from the $S_{cal}$ reference correlation line than from the $S_{hyp}$ error-compensated line. The $A_{corr}$ value obtained from the $S_{hyp}$ error-compensated line provides a more accurate value of the analyte concentration in the sample. Thus, Equation 1 translates a current value, $S_{cal}$, and Int into the compensated analyte concentration value $A_{corr}$ using ΔS. In this way, the percent bias may be linked through ΔS into Equation 1. The percent bias values may be pulled toward the center of a bias distribution through the linkage of ΔS to the percent bias. As ΔS is responsive to bias, changing ΔS affects the amount of bias remaining in the compensated analyte concentration of the sample.

If the value of ΔS is determined experimentally from samples and substituted into Equation 1, the bias in the determined analyte concentrations of those samples will be fully compensated. Alternatively, if ΔS is substituted with a predictor function, then the ability of the compensation equation to correct bias in the determined analyte concentration will depend on how well the value generated from the predictor function correlates with ΔS. In Equation 1, a predictor function, ƒ(predictor), may be substituted for ΔS. Thus, Equation 1 may be rewritten as follows:

$$A_{corr} = \frac{i - Int}{S_{cal} + \Delta S} = \frac{i - Int}{S_{cal} + f(\text{predictor})} = \frac{i - Int}{S_{cal} + b_1 * f(\text{Index}) + b_0}. \quad \text{(Equation 2)}$$

While the predictor function, ƒ(predictor), may have the general form of $b_1*f(\text{Index})+b_0$, other values or indices may be used in combination with the f(Index) to provide f(predictor). For example, the index function could be used with or without one or both of the $b_1$ and $b_0$ values to provide the predictor function. For the theoretical situation where ΔS and the index function perfectly correlate, $b_1$ (representing slope) and $b_0$ (representing intercept) are one and zero, respectively. Multiple index functions also may be combined to provide the ƒ(predictor), and thus, the corrected analyte concentration of the sample. Environmental and/or physical characteristics of the sample may be included in the predictor function, either as part of an index function, or otherwise. Similarly, secondary output signals may be included in the predictor function, either as part of an index function, or otherwise.

Slope deviation, ΔS, and/or related index functions may be normalized to represent the %-bias in the correlation of analyte concentrations with analytic output signals. Thus, the slope deviation, ΔS, in Equation 1 may be normalized by the slope of the reference correlation equation, $S_{cal}$, resulting in a compensation correlation between $\Delta S/S_{cal}$ and the index function. Additionally, normalized slope deviation may be expressed in multiple ways, such as by $\Delta S/S_{cal}$ or $S/S_{cal}$, where "S" represents any slope that deviates from $S_{cal}$. These expressions are equivalent, differing by 1, thus, $S/S_{cal}=1+\Delta S/S_{cal}$. The relationship where the normalized slope function $S_{NML}$ is replaced with an index function ƒ(Index) may be represented as follows:

$$A_{corr} = \frac{i - Int}{S_{cal} * (1 + \Delta S/S)} = \quad \text{(Equation 3)}$$
$$\frac{i - Int}{S_{cal} * S_{NML}} = \frac{i - Int}{S_{cal} * f(\text{Index})} = \frac{i - Int}{S_{cal} * (d_1 * \text{Index} + d_0)}.$$

Figure 5A:
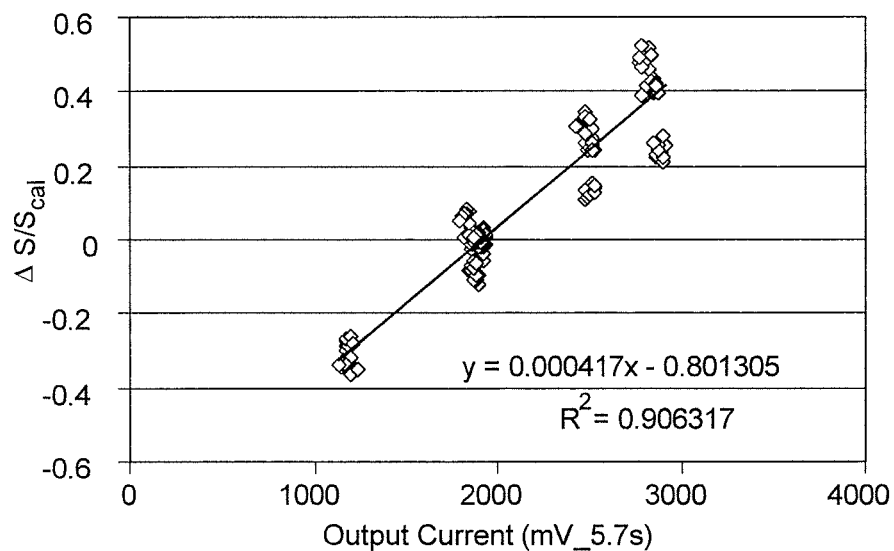
FIG. 5A shows the relationship between $\Delta S/S_{cal}$ and the secondary output signal currents (Hct) obtained from an additional electrode for multiple whole blood samples including different glucose concentrations and hematocrit contents of 0%, 20%, 45% and 70% Hct.

FIG. 5A shows the relationship between $\Delta S/S_{cal}$ and an index function including the secondary output signal currents obtained from an additional electrode (Hct). Multiple whole blood samples including different glucose concentrations and hematocrit contents of 0%, 20%, 45% and 70%-Hct were analyzed. The output current from the additional electrode was measured after about 5.7 seconds from the start of the analysis. The analyses were performed at about 25.3±0.5° C. A linear relationship having an $R^2$ value of about 0.91 was observed between $\Delta S/S_{cal}$ and the index function ((Index)=0.000417(Hct)−0.801305. Larger $R^2$ values reflect the index function being better at describing $\Delta S/S_{cal}$. From the correlation, a corrected glucose concentration $G_{corr}$ was determined using the equation as follows:

$$G_{corr}=(i-Int)/[S_{cal}*(1+f(\text{index})_{Hct})]=(i-Int)/[S_{cal}*(1+0.000417(Hct)-0.801305)] \quad \text{(Equation 4)},$$

where if Int is equal to or near 0, Int may be omitted from the equation.

Figure 5B:
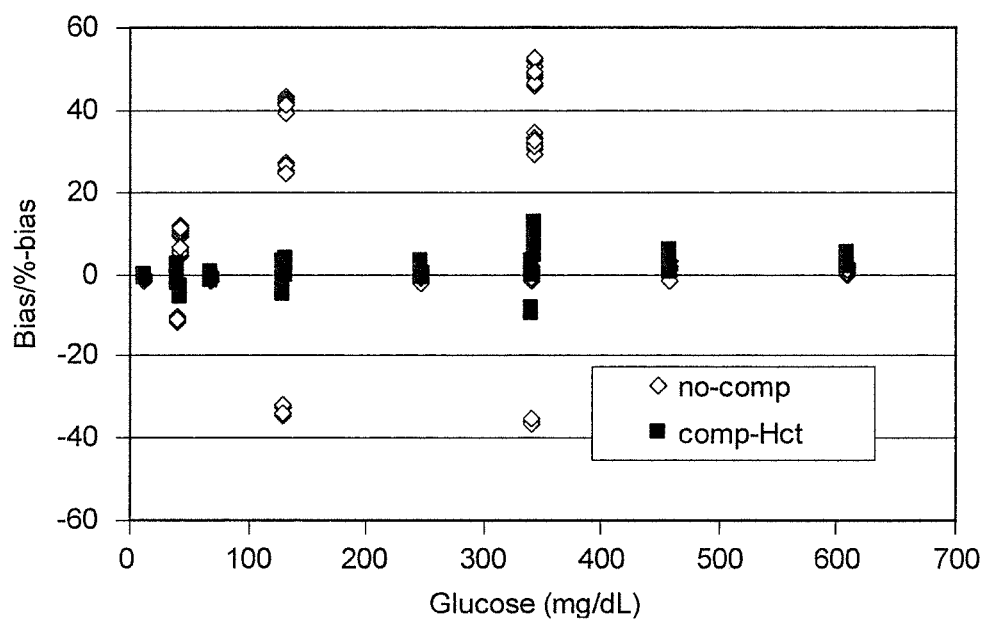
FIG. 5B shows the reduction in combined bias provided by the compensation.

FIG. 5B shows the reduction in combined bias provided by the compensation using the secondary output signal currents measured from the additional electrode. The compensation placed about 95% of the analyses within a ±10% combined bias limit.

Figure 5C:
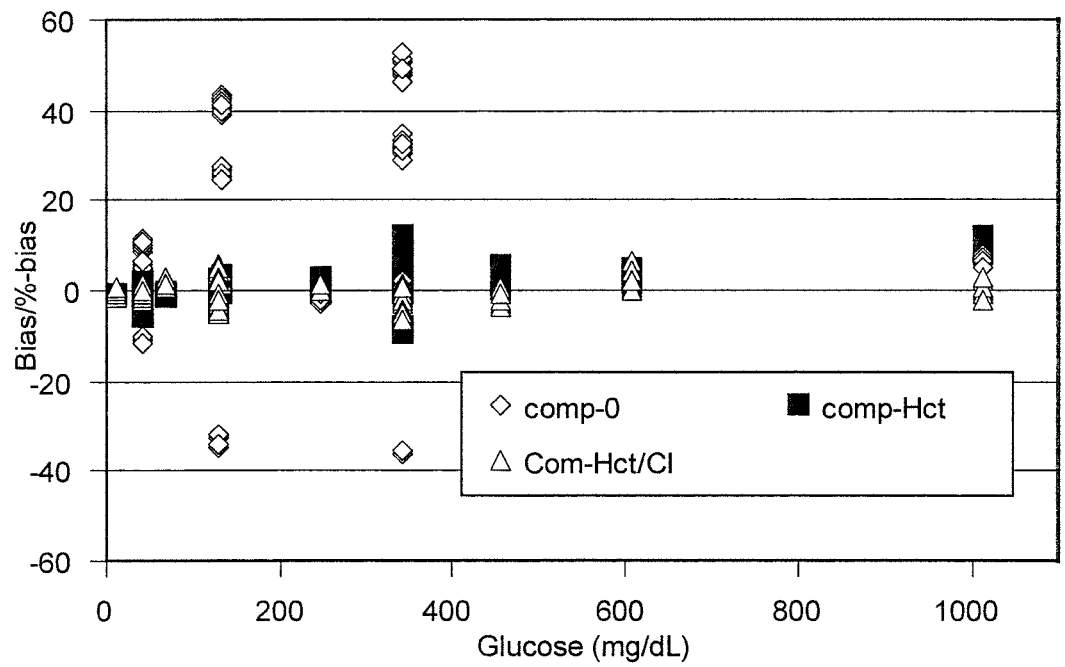
FIG. 5C compares the reduction in the combined biases resulting from slope compensation using different index functions for the same whole blood samples.

FIG. 5C compares the reduction in the combined biases resulting from slope compensation using different index functions for the whole blood samples used in FIG. 5A at 25° C. The graph shows the glucose concentrations determined from the uncorrected data (comp-0), the data corrected only with the combined ratio indices having cross terms with $G_{raw}$ (comp-R), with the secondary output currents obtained from an additional electrode (comp-Hct), and the data corrected with a complex index function including multiple ratio terms, additional electrode currents, and other error parameters (comp-Hct/R). Table 1, below, presents the percentage of the analyses falling within ±15.4, ±10.4, and ±5.4 combined bias limits. Table 1 also presents the results obtained from a complex index function including multiple ratio terms, but lacking error parameters from non-analytic output currents (comp-CI).

TABLE 1

| Compensation Comparison - Iso-thermal condition | | | |
|---|---|---|---|
| Compensation | ±15.4 | ±10.4 | ±5.4 |
| Comp-0 | 66.7 | 58.9 | 47.8 |
| Comp-R | 95.6 | 87.8 | 66.1 |
| Comp-Hct | 100 | 95 | 77.2 |
| Comp-Hct/R | 100 | 100 | 97.2 |

Without compensation, the analysis provided about 67% of the determined glucose concentrations within the approximately ±15% combined bias limit and about 48% of the glucose concentrations within the approximately ±5% combined bias limit. The complex index function alone and an index function using the current values from the additional electrode each increased the determined glucose concentrations within the bias limit. However, it was slope compensation using the combination of a complex index function including the additional electrode currents that significantly improved the ability of the biosensor system to provide glucose concentrations within the approximately ±5% combined bias limit.

While the biosensor system without compensation brought less than half of the analyses within the approximately ±5% combined bias limit, the Comp-Hct/CI correction method brought approximately 97% of the analyses within the approximately ±5% combined bias limit—a greater than 100% (97−48/48*100) improvement in measurement performance. By reducing the number of readings outside of the desired bias limit, more of the readings obtained could be used for accurate therapy by a patient when blood glucose is being monitored, for example. Additionally, the need to discard and repeat the analysis by the patient also may be reduced. For example, at a measurement performance cut-off of an approximately ±5% combined bias limit, a patient would have to discard and repeat only about 3% of the analyses performed from a glucose biosensor system using Comp-Hct/CI compensation. The same glucose biosensor system lacking compensation would require approximately 51% of the glucose analyses to be discarded at the approximately ±5% combined bias limit, rendering the uncompensated system effectively useless for achieving a measurement performance cut-off of an approximately ±5% combined bias limit.

Figure 6A:
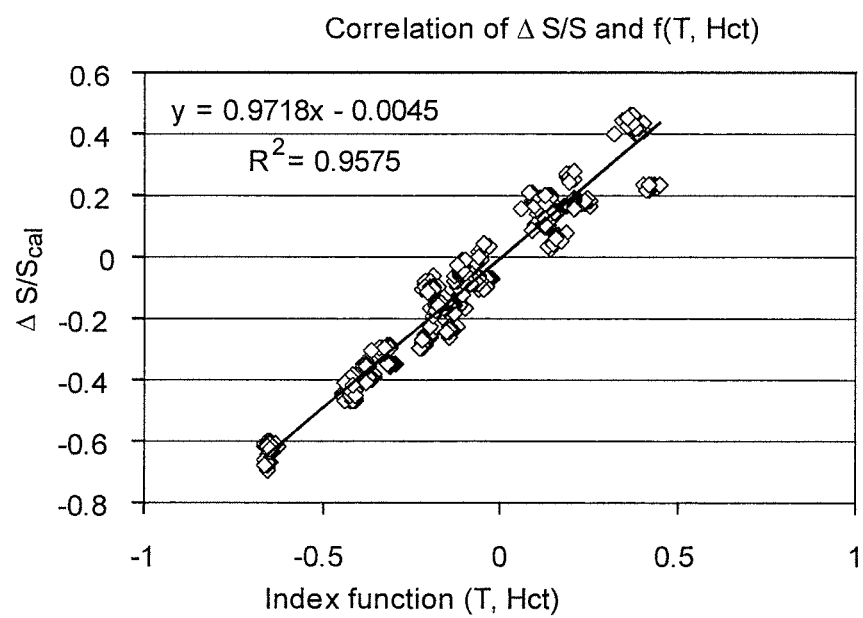
FIG. 6A shows the relationship between $\Delta S/S_{cal}$ and in index function including the secondary output signal currents obtained from an additional electrode (Hct) and temperature as error parameters.

FIG. 6A shows the relationship between $\Delta S/S_{cal}$ and an index function including the secondary output signal currents obtained from an additional electrode (Hct) and temperature as error parameters. Multiple whole blood samples including different glucose concentrations and hematocrit contents of about 0%, 20%, 45% and 70%-Hct were analyzed at about 15, 23, and 30° C. The current from the additional electrode was measured after about 7 seconds from the start of the analysis. A linear relationship having an $R^2$ value of about 0.96 was observed between $\Delta S/S_{cal}$ and the index function $f(\text{Index})_{T, Hct} = -1.27335 + 0.00038423 (\text{Hct}) + 0.0196054(\text{Temp}) + 0.00000189(\text{Temp})(\text{Hct})$. From the correlation, a corrected glucose concentration $G_{corr}$ was determined using either of following equations representing two forms of normalized slope deviation $\Delta S/S_{cal}$ and $S/S_{cal}$:

$G_{corr} = (i-\text{Int})/S_{cal} * [1+ f(\text{Index})_{T,Hct}] = i/S_{cal} * [1+(-1.27335+0.00038423(Hct)+0.0196054(\text{Temp})+0.00000189(\text{Temp})(Hct)]$  (Equation 5), and $G_{corr} = (i-\text{Int})/[S_{cal} * f(\text{Index})_{T,Hct}] = i/S_{cal}[-0.27335+0.00038423(Hct)+0.0196054(T)+0.00000189(T)(Hct)]$  (Equation 6), where if Int is equal to or near 0, Int may be omitted from the equation. The constant terms of the two index functions differ only by "1", and the remaining terms and their coefficients are identical.

Figure 6B:
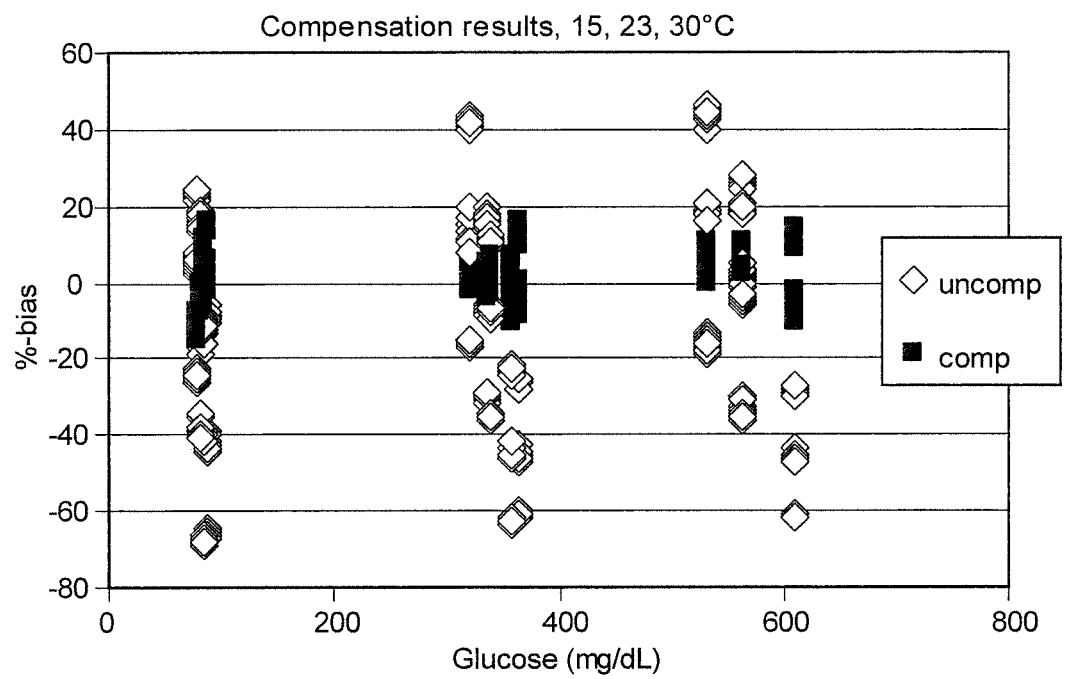
FIG. 6B shows the reduction in combined bias provided by the compensation with an index function using the secondary output signal currents measured from the additional electrode and temperature.

FIG. 6B shows the reduction in combined bias provided by the compensation with an index function using the secondary output signal currents measured from the additional electrode and temperature. The method placed about 93% of the 23° C. analyses, about 81% of the 30° C. analyses, and about 78% of the 15° C. analyses within a ±10% combined bias limit.

Since the secondary output signal currents from the additional electrode and the ratio indices are responsive to the hematocrit effect, adding the ratio indices to the index function may provide improved compensation of the hematocrit effect. A complex index function using temperature (Temp), secondary output signals from an additional electrode (Hct), and ratio indices extracted from the analytic output signals as terms was determined as follows for the same blood samples:

$f(\text{CIndex})_{T,HCT,Rx/y} = 6.0133 - 0.009708(Hct) + 0.84614(\text{Temp}) + 0.77235(R3/2) + 16.313(R4/3) - 19.912(R5/3) - 29.872(R6/5) + 25.376R6/4 - 0.012671(\text{Temp})(R3/2) - 1.03025(\text{Temp})(R5/4) + 0.12934(\text{Temp})(R5/3) - 0.6397(\text{Temp})(R6/5) + 0.72278(\text{Temp})(R6/4) - 6.0217e-4(Hct)(R3/2) - 0.015272(Hct)(R4/3) + 0.008254(Hct)(R5/4) + 0.016889(Hct)(R5/3) + 0.027849(Hct)(R6/5) - 0.026892(Hct)(R6/4)$  (Equation 7).

Figure 6C:
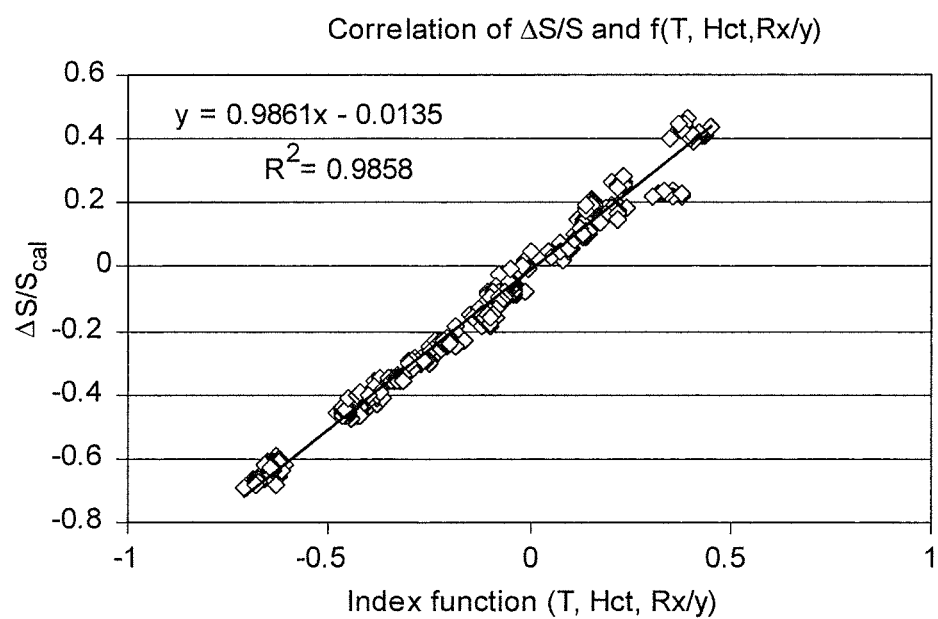
FIG. 6C depicts the correlation between a complex index function and $\Delta S/S_{cal}$.
Figure 6D:
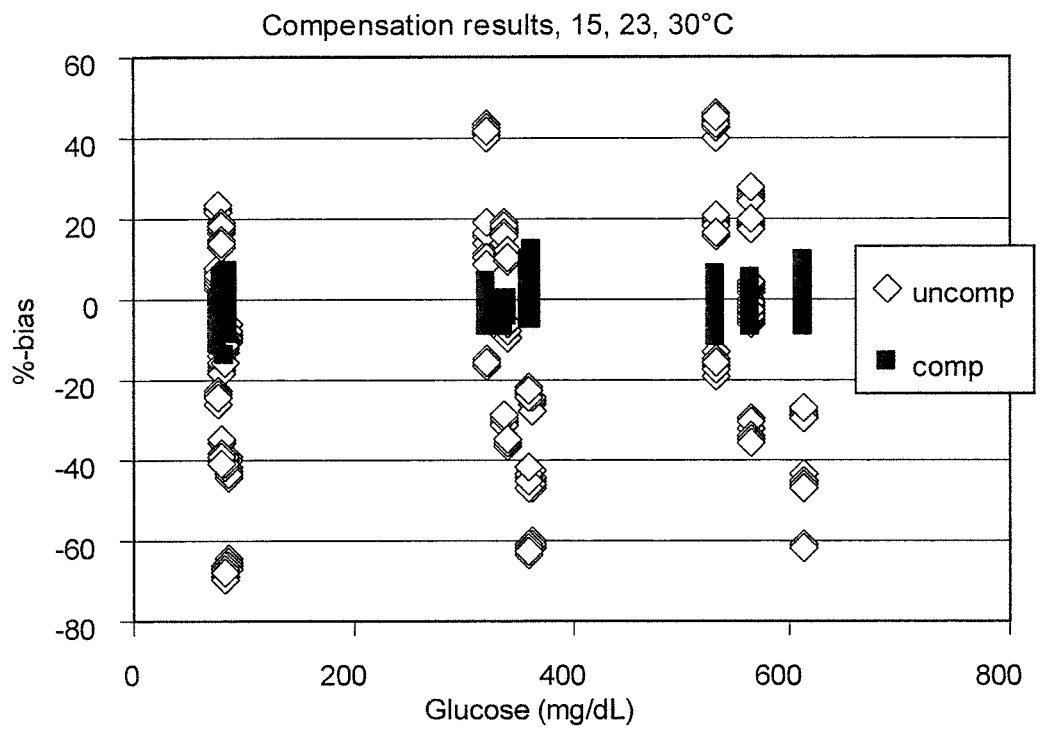
FIG. 6D shows the reduction in combined bias provided by compensation with a complex index function.

FIG. 6C depicts the correlation between the complex index function of Equation 7 and $\Delta S/S_{cal}$. The $R^2$ value reflecting how well the complex index values from the function correspond to the $\Delta S_{cal}$ values was 0.9858. FIG. 6D shows the reduction in combined bias provided by compensation with the complex index function of Equation 7. The method placed about 100% of the 23° C. analyses, about 98% of the 30° C. analyses, and about 98% of the 15° C. analyses within a ±10% combined bias limit.

The correlation between $\Delta S/S_{cal}$ and the index function may be improved by adding the raw glucose term $G_{raw}$ to the index function. A complex index function using temperature (Temp), secondary output signals from an additional electrode (Hct), ratio indices extracted from the analytic output signals, and $G_{raw}$ as terms was determined as follows for the same blood samples:

$f(\text{CIndex})_{T,HCT,Rx/y,Graw} = 27.407 - (0.0138549)(Hct) - (0.89007)(R4/3) - (23.859)(R5/4) - (28.142)(R6/5) + (24.517)(R6/4) + (3.7e-7)(Hct)(G_{raw}) - (0.010225)(R4/3)(G_{raw}) + (0.010064)(R5/3)(G_{raw}) + (0.009588)(R6/5)(G_{raw}) - (0.009867)(R6/4)(G_{raw}) + (5.07e-6)(\text{Temp})(Hct) + (0.037249)(\text{Temp})(R5/3) - (0.028559)(\text{Temp})(R6/5) + (0.0123729)(Hct)(R5/4) + (0.0146003)(Hct)(R6/5) - (0.0128883)(Hct)(R6/4)$  (Equation 8).

Figure 6E:
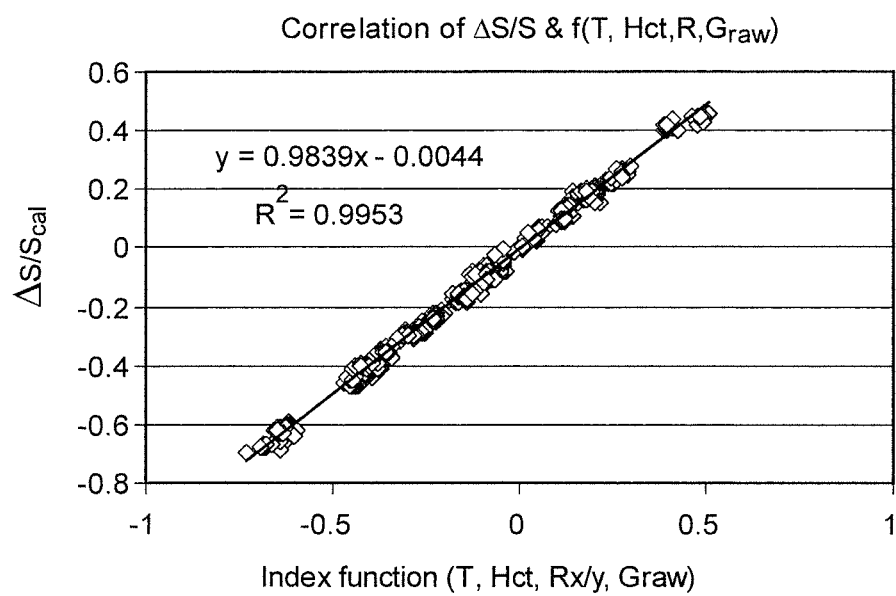
FIG. 6E depicts the correlation between a complex index function and $\Delta S/S_{cal}$.
Figure 6F:
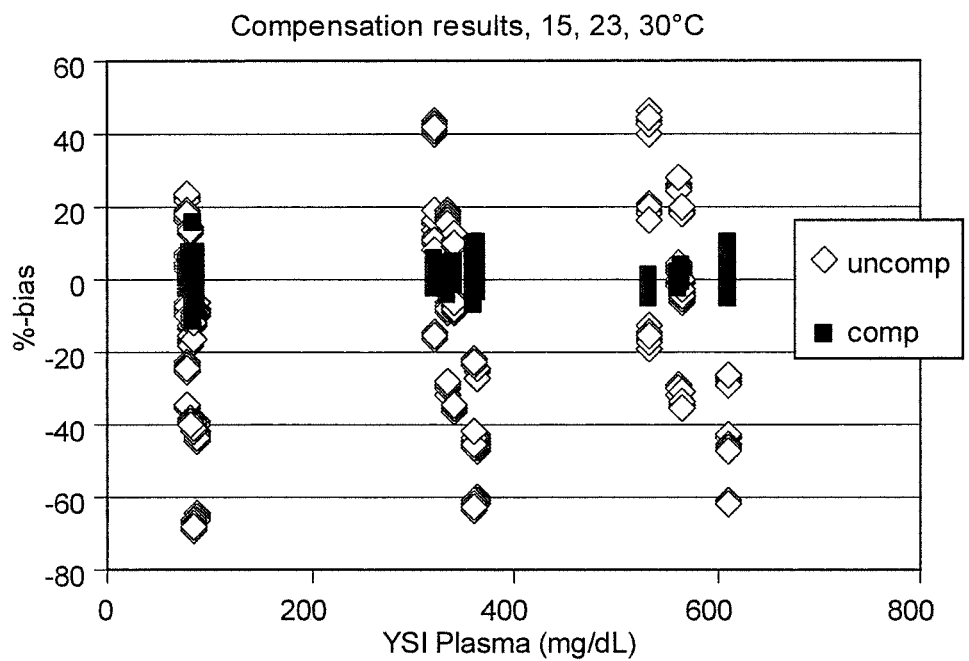
FIG. 6F shows the reduction in combined bias provided by compensation with a complex index function.

FIG. 6E depicts the correlation between the complex index function of Equation 8 and $\Delta S/S_{cal}$. The $R^2$ value reflecting how well the complex index values from the function correspond to the $\Delta S_{cal}$ values was 0.9953. FIG. 6F shows the reduction in combined bias provided by compensation with the complex index function of Equation 8. The method was able to place about 100% of the 23° C. analyses, about 100% of the 30° C. analyses, and about 98% of the 15° C. analyses within a ±10% combined bias limit. Table 2, below, compares the results from slope compensation with the index function of Equation 5 or Equation 6 and with the complex functions of Equation 7 and Equation 8 for the same blood samples.

TABLE 2

Compensation comparison - Temperature and Hematocrit

| Temperature, ° C. | Performance Criterion | Index function f(T, H) | Index function f(T, H, Rx/y) | Index function f(T, H, Rx/y, $G_{raw}$) |
|---|---|---|---|---|
| 23° C. | Mean %-bias | −0.137 | −1.160 | −0.684 |
|  | SD, %-bias | 6.014 | 3.409 | 2.566 |
|  | %-in ±10% | 93 | 100 | 100 |
|  | %-in ±5% | 47 | 84 | 94 |
| 30° C. | Mean %-bias | −0.083 | −1.345 | −0.525 |
|  | SD, %-bias | 7.488 | 3.627 | 2.052 |
|  | %-in ±10% | 81 | 98 | 100.0 |
|  | %-in ±5% | 46 | 88 | 98 |

TABLE 2-continued

Compensation comparison - Temperature and Hematocrit

| Temperature, °C. | Performance Criterion | Index function f(T, H) | Index function f(T, H, Rx/y) | Index function f(T, H, Rx/y, $G_{raw}$) |
|---|---|---|---|---|
| 15° C. | Mean %-bias | 1.514 | −0.753 | 1.483 |
| | SD, %-bias | 6.933 | 5.114 | 3.923 |
| | %-in ±10% | 78 | 98 | 98 |
| | %-in ±5% | 54 | 57 | 86 |
| Overall correlation with $\Delta S/S_{cal}$, $R^2$ | | 0.9575 | 0.9858 | 0.9953 |

At the ±10% combined bias limit, an improvement in measurement performance of about 26% (20/78*100) was observed at the lowest temperature of 15° C. with the addition of the ratio indices to the index function. At 23° C. and 30° C., improvements in measurement performance of about 21% (17/81*100) and about 8% (7/93*100) were respectively observed with the addition of the ratio indices to the index function. Thus, an average improvement in measurement performance of about 18% (26+21+8/3*100) was observed across the temperature range, with the greatest improvement being observed at lower temperatures. Additional improvement was observed through the inclusion of $G_{raw}$ and its cross terms in the index function.

At the ±5% combined bias limit, the index function lacking the ratio indexes could place less than 50% (47+46+54/3) of the analyses within the limit. Other than at 15° C., the addition of the ratio indexes nearly doubled the number of analyses within the ±5% combined bias limit, making this method suitable for use in a biosensor system providing the measurement performance of a ±5% bias limit. The addition of $G_{raw}$ and its cross terms provided continued improvement in the 23° and 30° C. analyses and brought the low temperature 15° C. analyses up to 86% within the ±5% combined bias limit. With an average analysis inclusion of about 93% (94+98+86/3) within the ±5% combined bias limit, the method including $G_{raw}$ and its cross terms in the index function would be more suitable for use in a biosensor system providing the measurement performance of a ±5% bias limit.

Figure 7A:
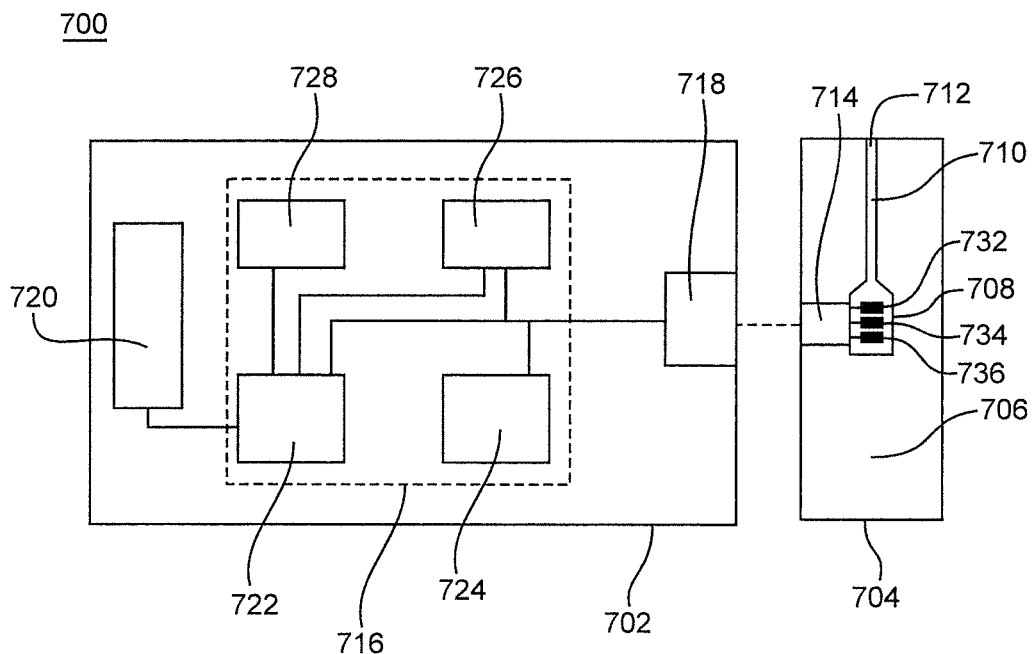
FIG. 7A depicts a schematic representation of a biosensor system that determines an analyte concentration in a sample of a biological fluid.

FIG. 7A depicts a schematic representation of a biosensor system 700 that determines an analyte concentration in a sample of a biological fluid. Biosensor system 700 includes a measurement device 702 and a test sensor 704, which may be implemented in any analytical instrument, including a bench-top device, a portable or hand-held device, or the like. The measurement device 702 and the test sensor 704 may be adapted to implement an electrochemical sensor system, an optical sensor system, a combination thereof, or the like. The biosensor system 700 adjusts a correlation for determining analyte concentrations from analytic and secondary output signals with at least one slope deviation value. The slope deviation adjusted correlations may improve the measurement performance of the biosensor system 700 in determining the analyte concentration of the sample. The biosensor system 700 may be utilized to determine analyte concentrations, including those of glucose, uric acid, lactate, cholesterol, bilirubin, and the like. While a particular configuration is shown, the biosensor system 700 may have other configurations, including those with additional components.

The test sensor 704 has a base 706 that forms a reservoir 708 and a channel 710 with an opening 712. The reservoir 708 and the channel 710 may be covered by a lid with a vent. The reservoir 708 defines a partially-enclosed volume. The reservoir 708 may contain a composition that assists in retaining a liquid sample such as water-swellable polymers or porous polymer matrices. Reagents may be deposited in the reservoir 708 and/or the channel 710. The reagents may include one or more enzymes, binders, mediators, and like species. The reagents may include a chemical indicator for an optical system. The test sensor 704 may have other configurations.

In an optical sensor system, a sample interface 714 has an optical portal or aperture for viewing the sample. The optical portal may be covered by an essentially transparent material. The sample interface 714 may have optical portals on opposite sides of the reservoir 708.

In an electrochemical system, the sample interface 714 has conductors connected to a working electrode 732 and a counter electrode 734 from which the analytic output signal may be measured. The sample interface 714 also may include conductors connected to one or more additional electrodes 736 from which secondary output signals may be measured. The electrodes may be substantially in the same plane or in more than one plane. The electrodes may be disposed on a surface of the base 706 that forms the reservoir 708. The electrodes may extend or project into the reservoir 708. A dielectric layer may partially cover the conductors and/or the electrodes. The sample interface 714 may have other electrodes and conductors.

The measurement device 702 includes electrical circuitry 716 connected to a sensor interface 718 and a display 720. The electrical circuitry 716 includes a processor 722 connected to a signal generator 724, an optional temperature sensor 726, and a storage medium 728.

The signal generator 724 provides an electrical input signal to the sensor interface 718 in response to the processor 722. In optical systems, the electrical input signal may be used to operate or control the detector and light source in the sensor interface 718. In electrochemical systems, the electrical input signal may be transmitted by the sensor interface 718 to the sample interface 714 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 724 also may record an output signal from the sensor interface as a generator-recorder.

The optional temperature sensor 726 determines the temperature of the sample in the reservoir of the test sensor 704. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 728 may be a magnetic, optical, or semiconductor memory, another storage device, or the like. The storage medium 728 may be a fixed memory device, a removable memory device, such as a memory card, remotely accessed, or the like.

The processor 722 implements the analyte analysis and data treatment using computer readable software code and data stored in the storage medium 728. The processor 722 may start the analyte analysis in response to the presence of the test sensor 704 at the sensor interface 718, the application of a sample to the test sensor 704, in response to user input, or the like.

The processor 722 directs the signal generator 724 to provide the electrical input signal to the sensor interface 718. The processor 722 receives the sample temperature from the temperature sensor 726. The processor 722 receives the output signal from the sensor interface 718. The output signal is generated in response to the reaction of the analyte in the sample. The output signal may be generated using an optical system, an electrochemical system, or the like. The processor 722 determines slope deviation compensated analyte concentrations from output signals using a correlation equation as previously discussed. The results of the analyte analysis may be output to the display 720 and may be stored in the storage medium 728.

The correlation equations between analyte concentrations and output signals may be represented graphically, mathematically, a combination thereof, or the like. A correlation equation may include one or more index functions. Correlation equations may be represented by a program number (PNA) table, another look-up table, or the like that is stored in the storage medium 728. Constants and weighing coefficients also may be stored in the storage medium 728. Instructions regarding implementation of the analyte analysis may be provided by the computer readable software code stored in the storage medium 728. The code may be object code or any other code describing or controlling the functionality described herein. The data from the analyte analysis may be subjected to one or more data treatments, including the determination of decay rates, K constants, ratios, functions, and the like in the processor 722.

In electrochemical systems, the sensor interface 718 has contacts that connect or electrically communicate with the conductors in the sample interface 714 of the test sensor 704. The sensor interface 718 transmits the electrical input signal from the signal generator 724 through the contacts to the connectors in the sample interface 714. The sensor interface 718 also transmits the output signal from the sample through the contacts to the processor 722 and/or signal generator 724.

In light-absorption and light-generated optical systems, the sensor interface 718 includes a detector that collects and measures light. The detector receives light from the liquid sensor through the optical portal in the sample interface 714. In a light-absorption optical system, the sensor interface 718 also includes a light source such as a laser, a light emitting diode, or the like. The incident beam may have a wavelength selected for absorption by the reaction product. The sensor interface 718 directs an incident beam from the light source through the optical portal in the sample interface 714. The detector may be positioned at an angle such as 45° to the optical portal to receive the light reflected back from the sample. The detector may be positioned adjacent to an optical portal on the other side of the sample from the light source to receive light transmitted through the sample. The detector may be positioned in another location to receive reflected and/or transmitted light.

The display 720 may be analog or digital. The display 720 may include a LCD, a LED, an OLED, a vacuum fluorescent, or other display adapted to show a numerical reading. Other displays may be used. The display 720 electrically communicates with the processor 722. The display 720 may be separate from the measurement device 702, such as when in wireless communication with the processor 722. Alternatively, the display 720 may be removed from the measurement device 702, such as when the measurement device 702 electrically communicates with a remote computing device, medication dosing pump, and the like.

In use, a liquid sample for analysis is transferred into the reservoir 708 by introducing the liquid to the opening 712. The liquid sample flows through the channel 710, filling the reservoir 708 while expelling the previously contained air. The liquid sample chemically reacts with the reagents deposited in the channel 710 and/or reservoir 708.

The test sensor 702 is disposed adjacent to the measurement device 702. Adjacent includes positions where the sample interface 714 is in electrical and/or optical communication with the sensor interface 718. Electrical communication includes the transfer of input and/or output signals between contacts in the sensor interface 718 and conductors in the sample interface 714. Optical communication includes the transfer of light between an optical portal in the sample interface 714 and a detector in the sensor interface 718. Optical communication also includes the transfer of light between an optical portal in the sample interface 714 and a light source in the sensor interface 718.

The processor 722 receives the sample temperature from the temperature sensor 726. The processor 722 directs the signal generator 724 to provide an input signal to the sensor interface 718. In an optical system, the sensor interface 718 operates the detector and light source in response to the input signal. In an electrochemical system, the sensor interface 718 provides the input signal to the sample through the sample interface 714. The processor 722 receives the output signal generated in response to the redox reaction of the analyte in the sample as previously discussed.

The processor 722 determines the analyte concentration of the sample. The measurement device adjusts the correlation between analyte concentrations and output signals with at least one slope deviation value. The analyte concentration is determined from the slope-adjusted correlation and the output signal. As described previously, normalization techniques also may be used.

While various embodiments of the invention have been described, it will be apparent to those of ordinary skill in the art that other embodiments and implementations are possible within the scope of the invention.

What is claimed is:

1. A method for determining an analyte concentration in a biological sample from a test sensor including a sample interface having a working electrode and a counter electrode, an additional sensor and a measurement device including a processor and a signal generator connected to the processor, the method comprising:
   applying an electrical input signal from the signal generator to the biological sample through the working electrode and the counter electrode of the sample interface;
   generating from the input signal an analytic output signal in response to a redox reaction of an analyte from the biological sample;
   generating a secondary output signal from the biological sample from the additional sensor, the secondary output signal in response to the hematocrit content of the sample, the secondary output signal being generated independently from the redox reaction of the analyte from the biological sample;
   measuring the temperature of the biological sample;
   determining at least one index function responsive to multiple error parameters via the processor, the index function including:
   a) at least one term based on values extracted from the analytic output signal,
   b) at least one term of the interaction based on the temperature measurement; and c) at least one term including the hematocrit content determined from the secondary output signal; and via the processor, determining the analyte concentration in the biological sample from the at least one analytic output signal and a slope compensation equation responsive to the at least one index function, wherein the slope compensation equation including at least one reference correlation between analyte concentrations and output signal values and at least one slope deviation from the reference correlation.

2. The method of claim 1, wherein the input signal includes a plurality of pulses, and wherein the index function includes at least one term of an individual ratio index based on values extracted from the analytic output signal.

3. The method of claim 2, wherein the index function includes at least one term of the interaction between at least one of the ratio indices based on values extracted from the analytic output signal, the temperature, the secondary output signal or determined analyte concentration of the sample without compensation.

4. The method of claim 1, wherein two of the terms include a weighing coefficient.

5. The method of claim 4, wherein the weighing coefficient is determined via statistical analysis from experimental data.

6. The method of claim 1, wherein the terms selected for inclusion in the index function are determined by an exclusion test from experimental data.

7. The method of claim 1 wherein the at least one slope deviation is responsive to a %-bias of the analyte concentration otherwise determined from the at least one output signal.

8. The method of claim 1, wherein the temperature is determined via a temperature sensor on the measurement device.

9. The method of claim 1, wherein a %-bias of the determined analyte concentration is either within ±10.4% or within ±5.4%.

10. The method of claim 1, wherein the biological sample is blood and the analyte is glucose.

11. A measurement device for determining an analyte concentration in a biological sample comprising:

a sensor interface coupleable to a sample interface of a test sensor having a reservoir for holding the biological sample, a counter electrode projecting into the reservoir, a working electrode projecting into the reservoir and an additional electrode projecting into the reservoir, wherein the sample interface includes conductors connected to the counter, working and additional electrodes;

a signal generator coupled to the sensor interface to generate an input signal through the sensor interface to the counter and working electrodes, and a secondary input signal through the sensor interface to the additional electrode;

a storage medium storing a slope compensation equation, a processor coupled to the sensor interface and the storage medium, wherein the processor operates to:

receive at least one analytic output signal in response to a redox reaction of an analyte from the biological sample;

receive a secondary output signal from the additional electrode, the secondary output signal in response to the hematocrit content of the sample, the secondary output signal being generated independently from the redox reaction of the analyte from the biological sample;

determine at least one index function responsive to multiple error parameters, the index function including:

a) at least one term of an individual ratio index based on values extracted from the analytic output signal, b) at least one term based on a temperature measurement of the biological sample, and c) at least one term including the hematocrit content determined from the at least one secondary output signal; and determine the analyte concentration in the biological sample from the at least one output signal and the slope compensation equation responsive to the at least one index function, the slope compensation equation including at least one reference correlation between analyte concentrations and output signal values and at least one slope deviation from the reference correlation.

12. The device of claim 11, wherein the input signal includes a plurality of pulses, and wherein the index function includes at least one term of an individual ratio index based on values extracted from the analytic output signal.

13. The device of claim 12, wherein the index function includes at least one term of the interaction between at least one of the ratio indices based on values extracted from the analytic output signal, the temperature, the secondary output signal or determined analyte concentration of the sample without compensation.

14. The device of claim 11, wherein two of the terms include a weighing coefficient.

15. The device of claim 14, wherein the weighing coefficient is determined via statistical analysis from experimental data.

16. The device of claim 11, wherein the terms selected for inclusion in the index function are determined by an exclusion test from experimental data.

17. The device of claim 11 wherein the at least one slope deviation is responsive to a %-bias of the analyte concentration otherwise determined from the at least one output signal.

18. The device of claim 11, further comprising a temperature sensor, and wherein the temperature is determined via the temperature sensor.

19. The device of claim 11, wherein a %-bias of the determined analyte concentration is either within ±10.4% or within ±5.4%.

20. The device of claim 11, wherein the biological sample is blood and the analyte is glucose.

* * * * *